(12) United States Patent
Krol et al.

(10) Patent No.: US 6,829,073 B1
(45) Date of Patent: Dec. 7, 2004

(54) OPTICAL READING SYSTEM AND METHOD FOR SPECTRAL MULTIPLEXING OF RESONANT WAVEGUIDE GRATINGS

(75) Inventors: Mark F. Krol, Painted Post, NY (US); Garrett A. Piech, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/689,453

(22) Filed: Oct. 20, 2003

(51) Int. Cl.[7] .................................................. G02F 1/03
(52) U.S. Cl. ........................ 359/263; 385/12; 385/37; 250/227.18
(58) Field of Search ..................... 250/227.11, 227.14, 250/227.18; 359/263; 385/12, 33, 37

(56) References Cited

U.S. PATENT DOCUMENTS

| | | | |
|---|---|---|---|
| 4,815,843 A | | 3/1989 | Tiefenthaler et al. ........ 356/128 |
| 5,089,387 A | * | 2/1992 | Tsay et al. ...................... 435/6 |
| 5,738,825 A | | 4/1998 | Rudigier et al. ......... 422/82.11 |
| 5,809,185 A | * | 9/1998 | Mitchell ....................... 385/12 |

OTHER PUBLICATIONS

K. Tiefenthaler et al., "Integrated Optical Switches and Gas Sensors", Optics Letters, vol. 10, No. 4, Apr. 1984, pp. 137–139.
W. Lukosz, "Integrated Optical Chemical and Direct Biochemical Sensors", Sensors and Actuators, vol. B, No. 29 (1995), pp. 37–50.
K. Tiefenthaler et al., "Sensitivity of Grating Couplers As Integrated–Optical Chemical Sensors", Journal Opt. Soc. Am. B, vol. 6, No. 2, Feb. 1989, pp. 209–220.

* cited by examiner

Primary Examiner—Hung Xuan Dang
Assistant Examiner—Tuyen Tra
(74) Attorney, Agent, or Firm—William J. Tucker; Thomas R. Beall

(57) ABSTRACT

An optical reading system is described herein which can be used to detect the presence of a biological substance (e.g., cell, drug, chemical compound) on a surface of a grating-based waveguide sensor. In one embodiment, the reading system includes a light source (e.g., laser, diode) for directing a light beam into the grating-based waveguide sensor and a detector (e.g., spectrometer, CCD imaging device) for receiving a reflected light beam from the grating-based waveguide sensor and analyzing the reflected light beam so as to detect a resonant wavelength/angle which corresponds to a predetermined refractive index that indicates whether a biological substance is located on the surface of the grating-based waveguide sensor. The grating-based waveguide sensor is tuned to have a resonant wavelength/angle at a predetermined spectral location by adjusting a skew angle defined as an angle between a plane of incidence of the light beam directed into the grating-based waveguide sensor and a grating vector which is perpendicular to the lines of a diffraction grating within the grating-based waveguide sensor. In another embodiment, the reading system is capable of performing a multiplexed interrogation of an array of grating-based waveguide sensors.

24 Claims, 7 Drawing Sheets

US 6,829,073 B1

OPTICAL READING SYSTEM AND METHOD FOR SPECTRAL MULTIPLEXING OF RESONANT WAVEGUIDE GRATINGS

BACKGROUND OF THE INVENTION

1. Field of the Invention

The present invention relates to an optical interrogation/reading system and method for detecting biological substances using one or more grating-based waveguide sensors (e.g., resonant waveguide gratings) that in one embodiment can be incorporated within a microplate.

2. Description of Related Art

Today studies associated with detecting a biological substance (e.g., cell, drug, chemical compound) using resonant waveguide gratings (RWGs) are fast becoming the technology of choice in academia and industry. In such studies, a reading system is used to couple light into the RWG and also used to analyze the light that is reflected from the RWG in order to determine whether or not a biological substance is present on the surface of the RWG. To detect the biological substance, the reading system analyzes the reflected light to locate its resonant wavelength/angle which corresponds to a certain refractive index that is indicative of whether or not the biological substance is located on the surface of the grating-based waveguide sensor. Unfortunately, the reading system used in industry today suffers from a major drawback wherein it is difficult for a user to tune the RWG and reading system so that the reading system can properly interface with the RWG. In particular, it is difficult for a user to tune the RWG so that its resonant wavelength/angle is at a desired spectral location so that the resonant wavelength/angle can be easily detected by the reading system. This drawback is especially troublesome when a multi-channel reading system is used to interface in a multiplexed manner with an array of RWGs. Accordingly, there is a need for a way to make it easier to tune a reading system and RWG to address the aforementioned shortcoming and other shortcomings in the prior art. This need and other needs are satisfied by the reading system, RWG and method of the present invention.

BRIEF DESCRIPTION OF THE INVENTION

The present invention includes a reading system and at least one grating-based waveguide sensor that interact with one another to enable the detection of biological substances (e.g., cells, drugs, chemical compounds). In one embodiment, the reading system includes a light source (e.g., laser, diode) for directing a light beam into the grating-based waveguide sensor and a detector (e.g., spectrometer, CCD imaging device) for receiving a reflected light beam from the grating-based waveguide sensor and analyzing the reflected light beam so as to detect a resonant wavelength/angle which corresponds to a predetermined refractive index that indicates whether a biological substance is located on the surface of the grating-based waveguide sensor. The grating-based waveguide sensor is tuned to have a resonant wavelength/angle at a predetermined spectral location by adjusting a skew angle defined as an angle between a plane of incidence of the light beam directed into the grating-based waveguide sensor and a grating vector which is perpendicular to the lines of a diffraction grating within the grating-based waveguide sensor. In another embodiment, the reading system is capable of performing a multiplexed interrogation of an array of grating-based waveguide sensors.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
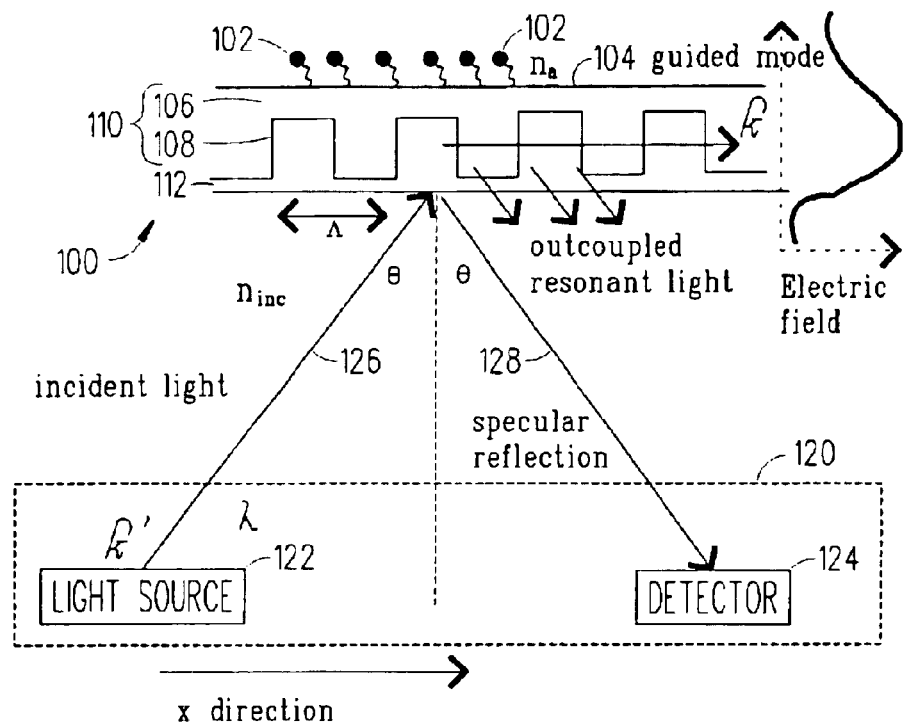
FIG. 1 is a diagram of the basic components of a reading system and RWG in accordance with the present invention.

Referring to FIG. 1, there is shown a diagram of the basic components of a RWG 100 and a reading system 120 in accordance with the present invention. Basically, the RWG 100 is a grating-based waveguide sensor which makes use of the refractive and coupling properties of light emitted from the reading system 120 and then reflected back into the reading system 120 which is used to enable label-free detection of a biological substance 102 (e.g., cell, molecule, protein, drug, chemical compound, nucleic acid, peptide, carbohydrate) on a surface 104 of the RWG 100. The reading system 120 includes one or more light sources 122 (e.g., laser, diodes) and one or more detectors 124 (e.g., spectrometers, CCD cameras or other imaging detectors).

The RWG 100 includes a thin (~100 nm) layer of material 106 (e.g., waveguide film 106) deposited on the surface of a diffraction grating 108 which together form a waveguide 110. The waveguide film 106 is preferably made of a metal-oxide based material such as $Ta_2O_5$, $TiO_2$, $TiO_2$—

SiO$_2$, HfO$_2$, ZrO$_2$, Al$_2$O$_3$, Si$_3$N$_4$, HfON, SiON, scandium oxides or mixtures thereof. The diffraction grating 108 is formed within a substrate 112 by embossing, holography, or other methods and then the thin waveguide film 106 having a higher refractive index is coated on top of the diffraction grating 108. The substrate 112 is preferably made of glass or plastic such as cyclo-olefin.

The biological substance 102 which may be located within a bulk fluid is deposited on top of the surface 104 and it is the presence of this biological substance 102 that alters the index of refraction at the surface 104 of the RWG 100. Thus, to detect the biological substance 102, the RWG 100 is probed with a light beam 126 emitted from the light source 122 and then a reflected light beam 128 received at the detector 124 is analyzed to determine if there are any changes (~1 part per million) in the refractive index caused by the addition of the biological substance 102 at the surface 104 of the RWG 100. In one embodiment, the surface 104 may be coated with biochemical compounds (not shown) that only allow surface attachment of specific complementary biological substances 102 which enables a RWG 100 to be created that is both highly sensitive and highly specific. In this way, the reading system 120 and RWGs 100 may be used to detect a wide variety of biological substances 102 and if the RWGs 100 are arranged in arrays they may be used to enable high throughput drug or chemical screening studies. A more detailed discussion about the basics of an RWG is provided in U.S. Pat. No. 4,815,843 the contents of which are incorporated by reference herein.

The sensitivity of the RWG 100 may be best understood by analyzing the structure of the diffraction grating 108 and the waveguide 110. For the fundamental waveguide mode, the light beam 126 shone on the diffraction grating 108 can only be coupled into the waveguide 110 if its wave vector satisfies the following resonant condition as shown in equation no. 1:

$$k_x' = k_x - \kappa \qquad [1]$$

where $k_x'$ is the x-component of the incident wave vector, $k_x$ is the guided mode wave vector, and $\kappa$ is the grating vector. The grating vector $\kappa$ is defined as a vector having a direction perpendicular to the lines of the diffraction grating 108 and a magnitude given by $2\pi/\Lambda$ where $\Lambda$ is the grating period (pitch)(see FIG. 5). This expression may also be written in terms of wavelength $\lambda$ and incident angle $\theta$ as shown in equation no. 2:

$$\frac{2\pi n_{inc}}{\lambda} \sin\theta = \frac{2\pi n_{eff}}{\lambda} - \frac{2\pi}{\Lambda} \qquad [2]$$

Where $\theta$ is the angle of incidence, $n_{inc}$ is the index of refraction of the incident medium, $\lambda$ is the wavelength of the light 126, and $n_{eff}$ is the effective index of refraction of the waveguide 110. The effective index of the waveguide 110 is a weighted average of the indices of refraction that the optical waveguide mode field "sees" as it propagates through the waveguide 110. The guided mode may have a spatial extent that is much wider than the waveguide 110 itself, the extent depending on the index difference and specific geometric design of the waveguide 110. In particular, the fundamental mode has an evanescent wave/tail that extends into the cover medium (sensing region) which "sees" any surface changes created when the biological substance 102 approaches or comes in contact with the surface 104 of the RWG 100.

Figure 2:
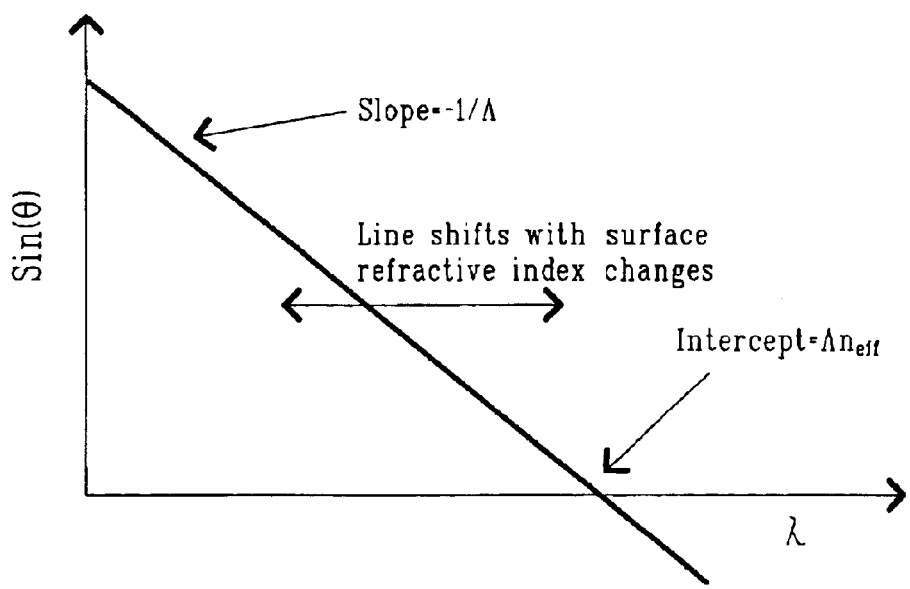
FIG. 2 is a graph that illustrates the relationship between the resonant angle and resonant wavelength of the RWG shown in FIG. 1.

The previous expression shown in equation no. 2 may be rewritten in the more convenient form shown in equation no. 3:

$$\sin\theta = n_{eff} - \frac{\lambda}{\Lambda} \qquad [3]$$

which is the equation of a line where sin $\theta$ being the y axis, $\lambda$ being the x-axis, $\Lambda n_{eff}$ the x-intercept, and $-1/\Lambda$ the slope. To obtain equation no. 3, $n_{inc}$ has been set to 1 so that it could be removed from this expression, simplifying this and subsequent expressions. This approximation is used since air (n~1.0003) is the most common incident medium. It should be understood that this approximation does not reduce the generality of the results of this analysis. This relation is pictured in the graph shown in FIG. 2. When a biological substance 102 binds to the surface 104, the effective index of the waveguide 110 is altered which leads to the shifting the resonant wavelength or resonant angle of the RWG 100. This shifting can be seen as a shift of the x-intercept in the line shown in FIG. 2. A more detailed discussion about the basics of the resonant conditions associated with an RWG is provided in the following articles: (1) K. Tiefenthaler et al. entitled "*Integrated Optical Switches and Gas Sensors*" Opt. Lett. 10, No. 4, April 1984, pp.137–139; (2) K. Tiefenthaler et al. entitled "*Sensitivity of Grating Couplers as Integrated-Optical Chemical Sensors*" J. Opt. Soc. Am. B 6, No. 2, Feb. 1989, pp. 209–220; and (3) W. Lukosz entitled "*Integrated Optical Chemical and Direct Biochemical Sensors*" Sensors and Actuators B 29, 1995, pp.37–50. The contents of these three articles are incorporated by reference herein.

Figure 3:
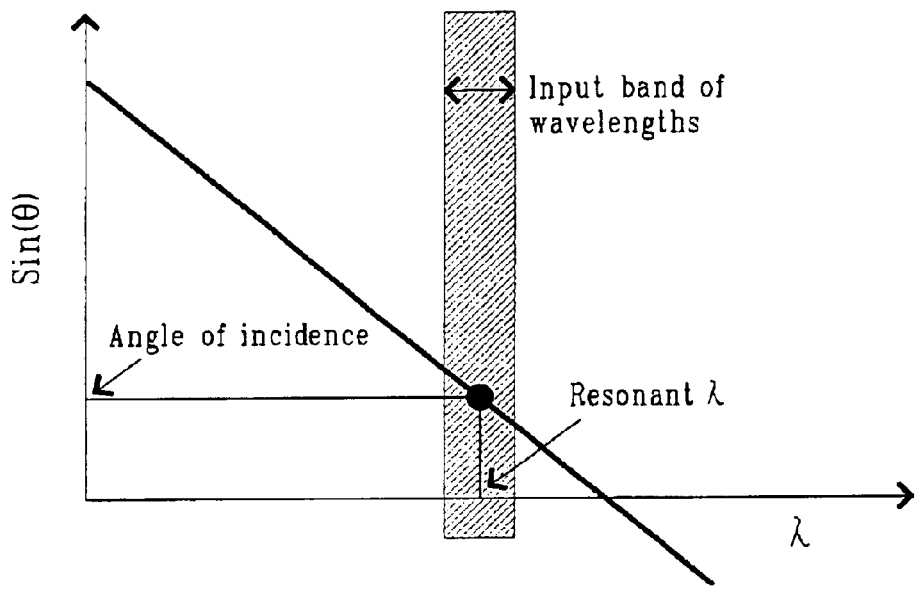
FIG. 3 is a graph used to help describe how a spectral interrogation approach can be used by the reading system to determine the resonant wavelength of the RWG shown in FIG. 1.
Figure 4:
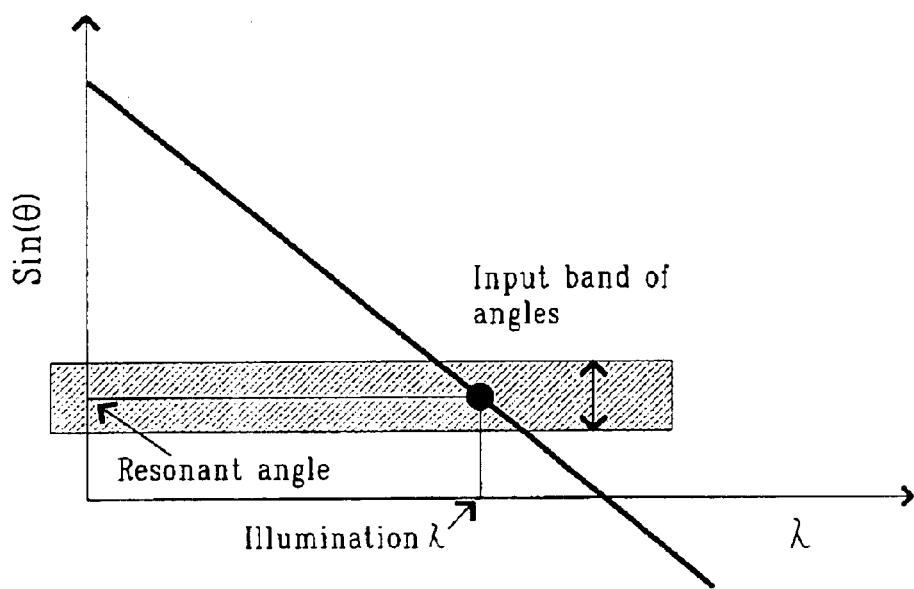
FIG. 4 is a graph used to help describe how an angular interrogation approach can be used by the reading system to determine the resonant angle of the RWG shown in FIG. 1.

The resonant condition (e.g., resonant wavelength or resonant angle) of such a RWG 100 may be interrogated to determine refractive index changes by observing the reflected light 128 from the RWG 100 (see FIG. 1). There are two different modes of operation for monitoring refractive index changes-spectral interrogation or angular interrogation. In spectral interrogation, a nominally collimated, broadband beam of light 126 is sent into the RWG 100 and the reflected light 128 is collected and monitored with a spectrometer 124 (for example). By observing the spectral location of the resonant wavelength (peak), one can monitor binding or refractive index changes at or near the surface 104 of the RWG 100. The spectral interrogation concept is graphically represented in the graph shown in FIG. 3. Conversely, in angular interrogation, a nominally single wavelength of light 126 is focused to create a range of illumination angles and directed into the RWG 100. The reflected light 128 is monitored with a CCD camera or other imaging detector 124. By monitoring the position of the resonant angle reflected by the RWG 100, one can monitor binding or refractive index changes at or near the surface 104 of the RWG 100. The angular interrogation concept is graphically represented in the graph shown in FIG. 4.

Figure 5:
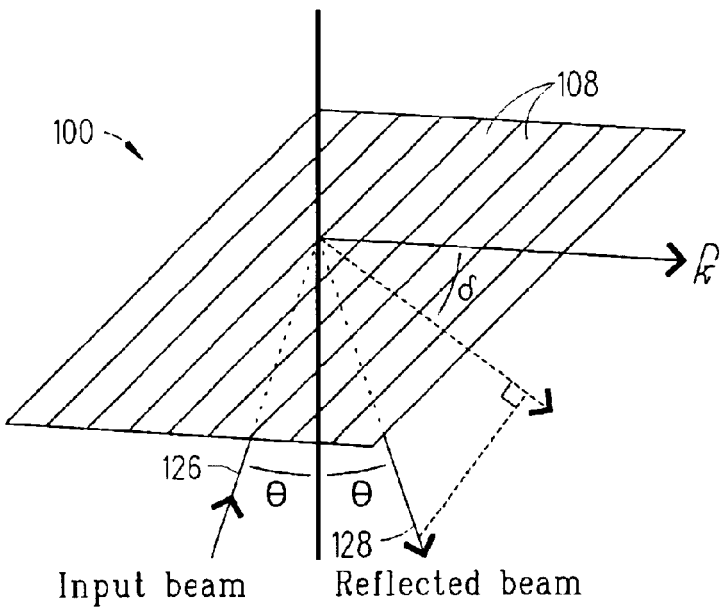
FIG. 5 is a diagram illustrating how an incident light beam emitted from the reading system can be skewed with respect to a grating vector κ of the RWG shown in FIG. 1 in accordance with the present invention.

In accordance with the present invention if the plane of the incidence of the light beam 126 is skewed with respect to the grating vector K, then equation no. 3 may be rewritten as equation no. 4:

$$\sin\theta\cos\delta = n_{eff} - \frac{\lambda}{\Lambda} \qquad [4]$$

where $\delta$ is the skew angle which is depicted in FIG. 5. The skew angle $\delta$ is defined as an angle between a plane of incidence the light beam 126 directed into the RWG 100 and the grating vector K which is perpendicular to lines of the diffraction grating 108 within the RWG 100. It should be noted that there are two solutions to equation no. 4, one for positive angles and one for negative angles. These solutions correspond physically to waveguide modes propagating in the ±x direction (see FIG. 1). Writing equations for both of these solutions using ±θ results in equation no. 5:

$$\sin\theta\cos\delta = n_{eff} - \frac{\lambda^-}{\Lambda} \qquad [5]$$

$$\sin\theta\cos\delta = -n_{eff} + \frac{\lambda^+}{\Lambda}$$

If the RWG 100 is interrogated spectrally, then it is helpful to re-express equation no. 5 in terms of the resonant wavelength $\lambda^-$ and $\lambda^+$ shown in equation no. 6:

$$\lambda^{\pm} = \Lambda n_{eff} \pm \Lambda\sin\theta\cos\delta \qquad [6]$$

It should be noted that for light 126 shone with a normal incidence (θ=0), the dual resonances $\lambda^-$ and $\lambda^+$ occur at the same wavelength and adjusting the skew angle δ will have no effect. However, for θ≠0, the two resonances $\lambda^-$ and $\lambda^+$ exist, with a separation Δλ represented in equation no. 7:

$$\Delta\lambda = 2\Lambda\sin\theta\cos\delta \qquad [7]$$

Rotating the skew angle δ moves the dual resonances $\lambda^-$ and $\lambda^+$ closer to one another or further apart from one another, with the maximum separation $\Delta\lambda_{max}$ represented in equation no. 8:

$$\Delta\lambda_{max} = 2\Lambda\sin\theta \qquad [8]$$

Figure 6:
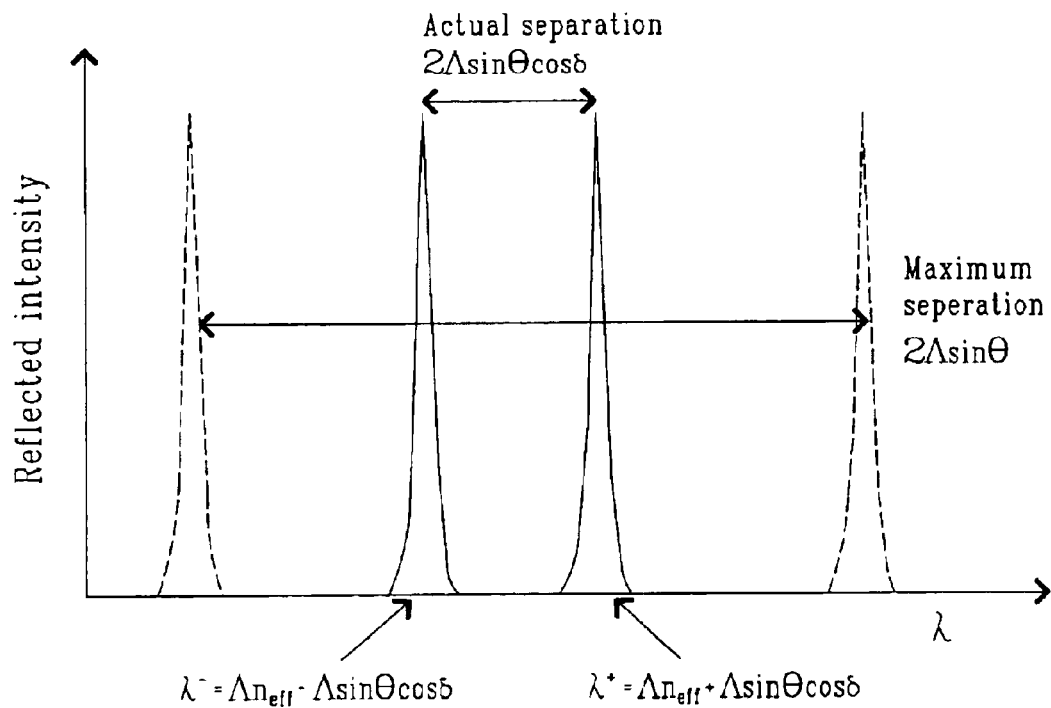
FIG. 6 is a graph illustrating the spectral positions of the resonant wavelengths $\lambda^-$ and $\lambda^+$ of the RWG shown in FIGS. 1 and 5.

This situation is depicted in FIG. 6. Adjustment of the skew angle δ allows one to control the spectral position of the individual resonances $\lambda^-$ and $\lambda^+$. Even if identical RWGs 100 are illuminated with light 126 having the same angle of incidences θ, one may spectrally separate the resonant signals $\lambda^-$ and $\lambda^+$ from each other by striking each of the RWGs 100 with light 126 at a different angle skew angle δ. Adjustment of the skew angle δ provides at least two advantages to system design. First, it allows one to tune an individual resonance $\lambda^+$ or $\lambda^+$ to a more convenient location for the reading system 120. This could allow one to place the resonance $\lambda^-$ or $\lambda^+$ at a spectral location with more power, or at a location that enables one to maximize the dynamic range of a particular reading system 120. Second, the use and control of skew angles δs with multiple RWGs 100 provides a way to adjust the spectral locations of the resonance signals $\lambda^-$ and $\lambda^+$ for each of the RWGs 100 and hence enable spectral multiplexing of multiple reflected light beams 128. The multiple reflected light beams 128 may be combined in free space or via fiber optics and fed into a single channel of a spectrometer 124 or other dispersive device 124 (see FIGS. 9 and 10).

In accordance with the present invention, the skew angle δ may be controlled by rotating the physical diffraction grating 108 in the RWG 100 with respect to the plane defined by the incident light beam 126 and the reflected light beam 128 (see FIG. 5). If the plane of the incidence of light 126 is held constant, this rotation could be performed by manufacturing an array of RWGs 100 where each RWG 100 has diffraction gratings 108 that are oriented with a precisely defined skew angle δ. Such an arrangement may be suitable if a set of free space optical light beams 126, such as that formed by a system of lenses, micro-optics, or diffractive optics is used to illuminate the RWGs 100. Since it may not be easy to adjust the skew angle δ using the optics of such a setup, pre-fabricating the RWGs 100 to have diffraction gratings 108 with defined skew angles δs may provide the most efficient path toward manipulating the location of the resonant signals $\lambda^-$ and $\lambda^+$.

Figure 7:
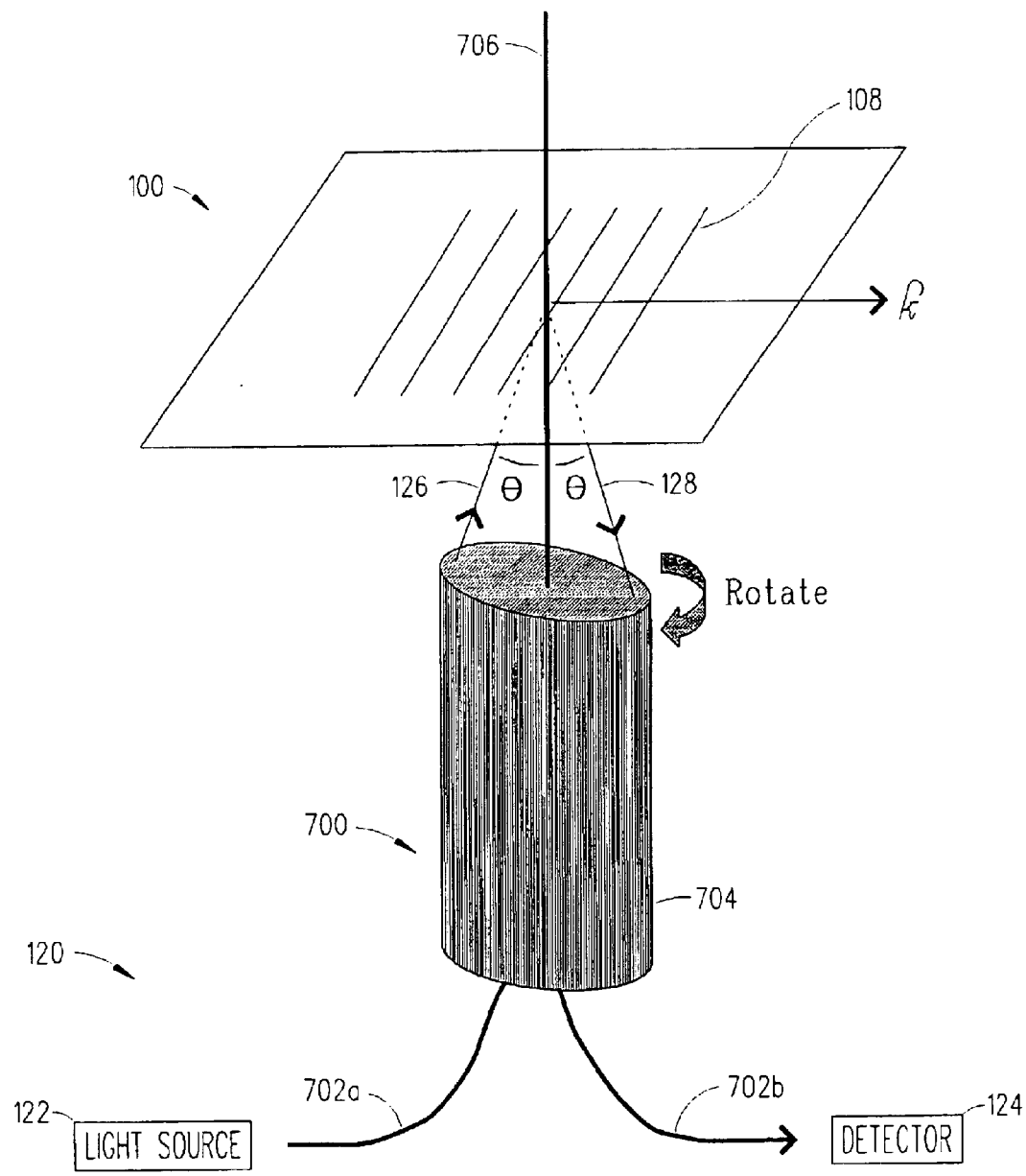
FIG. 7 is a diagram illustrating one embodiment of the reading system shown in FIG. 1 that has a dual fiber gradient index (GRIN) lens package which can be rotated to control the skew angle δ between the incident light beam and the grating vector K in the RWG.
Figure 8A:
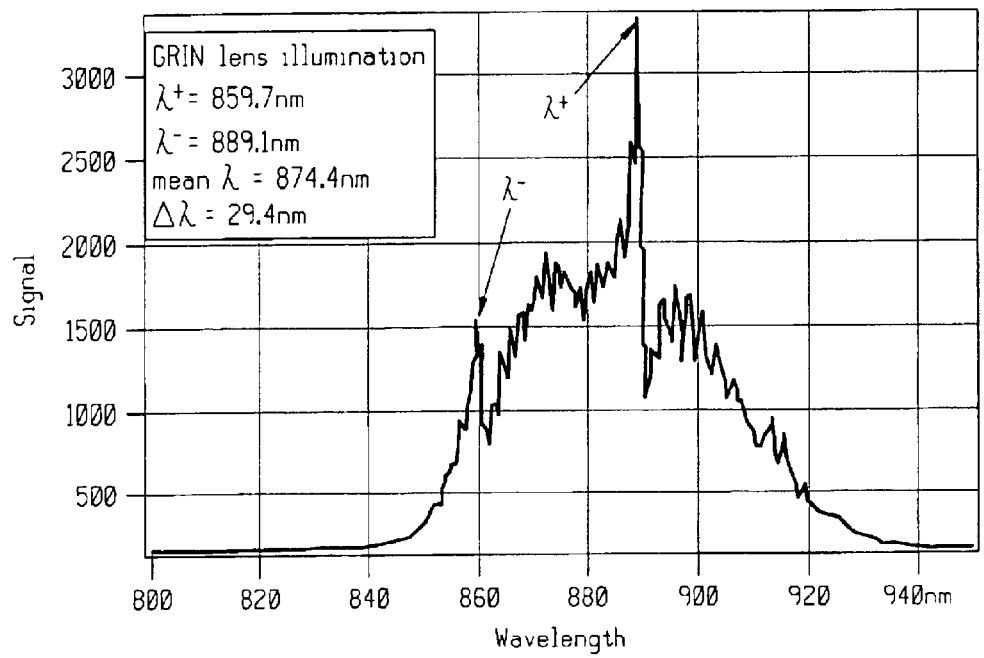
FIG. 8A is a graph illustrating a double resonance wavelength $\lambda^-$ and $\lambda^+$ that was observed when the reading system and GRIN lens package shown in FIGS. 1 and 7 interfaced with the RWG at a 36° skew angle.
Figure 8B:
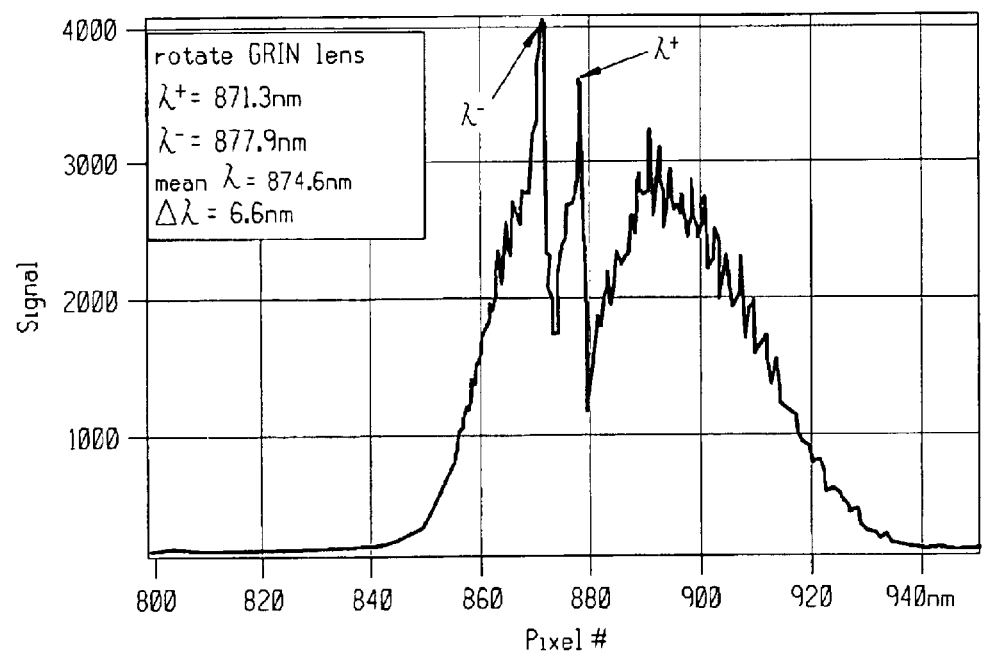
FIG. 8B is a graph illustrating a double resonance wavelength $\lambda^-$ and $\lambda^+$ that was observed when the reading system and GRIN lens package shown in FIGS. 1 and 7 interfaced with the RWG at a 80° skew angle.

If fiber optics are used to emit light 126 into the RWGs 100 and collect the reflected light 128 from the RWGs 100, then it may be easier to fabricate RWGs 100 with a uniform set of diffraction gratings 108 that are oriented in the same direction and then rotate the illumination fiber optics relative to each of the RWGs 100 to obtain the desired skew angles δs. For example as shown in FIG. 7, if dual fiber gradient index (GRIN) lenses 700 are used, the plane containing the two fibers 702a and 702b in the package/canister 704 defines the plane of incidence. Rotation of the plane of incidence may be easily accomplished by rotating the canister 704 holding the GRIN lens about an axis 706 normal to the diffraction grating 108 in the RWG 100. Graphs illustrating the results of rotating such a GRIN lens system 700 that emits light 126 having an angle of incidence θ of 1.94° are shown in FIGS. 8A and 8B. One can see that the spacing of the dual resonances $\lambda^-$ and $\lambda^+$ changed from Δλ=29.4 nm when δ =36° in the example shown in FIG. 8A to 6.6 nm when the lens 700 was rotated to have a skew angle corresponding to δ=80° shown in FIG. 8B. It should be noted that the mean location of the two resonances $\lambda^-$ and $\lambda^+$ is given by $\lambda = \Lambda n_{eff}$ and that the mean location remains the same no matter what angle of incidence θ and skew angle δ are chosen. It should also be noted that the use of skew angle δ to control the location of the resonance location $\lambda^-$ and $\lambda^+$ may be used whether or not the double resonance phenomenon is utilized, since the skew angle δ affects both resonances $\lambda^-$ and $\lambda^+$ as seen in equation no. 6.

Figure 9A:
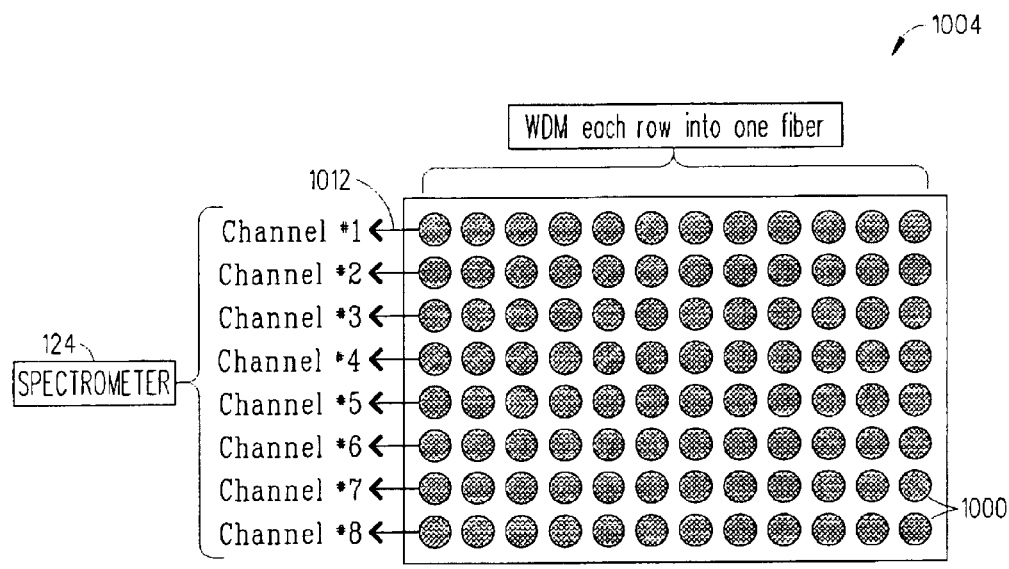
FIGS. 9A and 9B illustrate a top view and cross-sectional side view of a microplate that has wells the bottom of which include RWGs that interface with one embodiment of the reading system shown in FIG. 1.
Figure 9B:
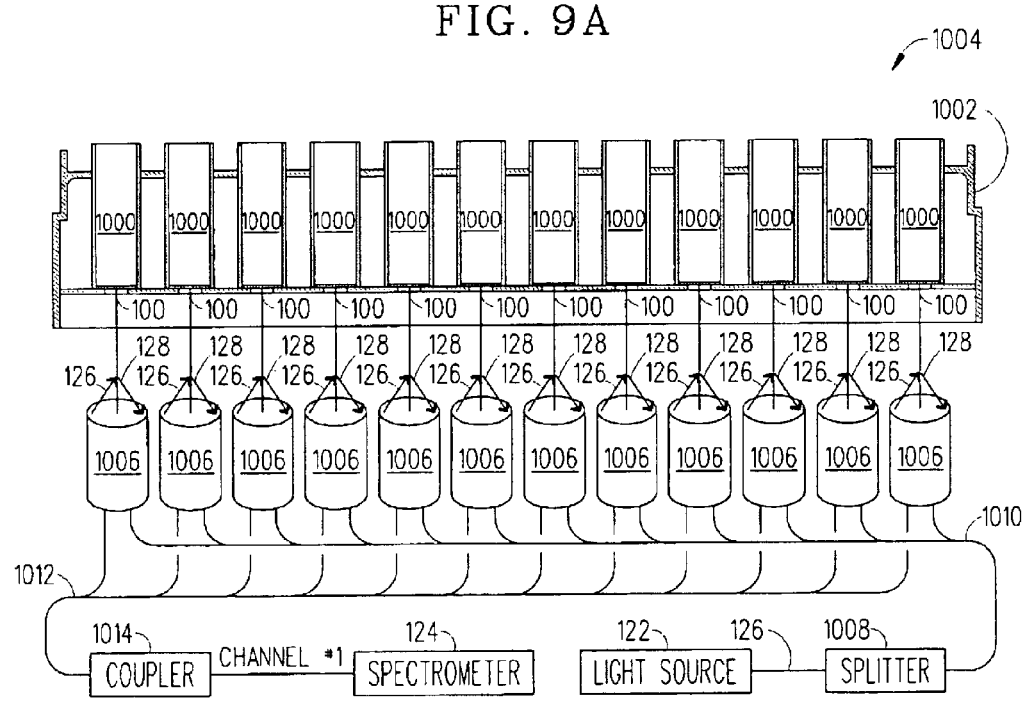

In order to spectrally multiplex the reflected signals 128 from multiple RWGs 100, one needs to connect the collected reflected light beams 128 together which can in one example be accomplished by using fiber couplers. For example, an array of RWGs 100 may be incorporated within the bottoms of wells 1000 formed within a frame 1002 of a microplate 1004 as shown in FIGS. 9A and 9B. In one embodiment, dual fiber collimator lenses 1006 similar to lenses 700 shown in FIG. 7 are located below each well 1000. And, the light source 122 is coupled to fiber splitter(s) 1008 which split the source light 126 into a row of input fibers 1010 connected to the fiber collimator lenses 1006 (see FIG. 9B). Each fiber collimator lens 1006 is oriented to have a specific and unique skew angle δ with respect to the diffraction grating 108 within the RWG 100 it interrogates (see FIG. 7). Thus, each resonance $\lambda^-$ and/or $\lambda^+$ of the RWGs 100 is pre-tuned to a specific spectral region within the optical band of the light source 122. Again, the RWGs 100 in this example can all have diffraction gratings 108 with the same orientation. The reflected light beams 128 are directed into the corresponding output fibers 1012 of the fiber collimator lenses 1006. The output fibers 1012 associated with a row are then spliced together by a coupler 1014 and sent into a single channel of a spectrometer 124. As such, a single channel can collect reflected signals 128 from multiple RWGs 100 simultaneously, avoiding the need to manufacture RWGs 100 with different angled diffraction gratings 108, or the need for time division multiplexing techniques where optical switches, multiple sources, or optics scanning (translation) is used to read multiple RWGs 100. An illustration of how the spectrum of a single channel might look for such a multiplexed system is shown in FIG. 10.

Figure 10:
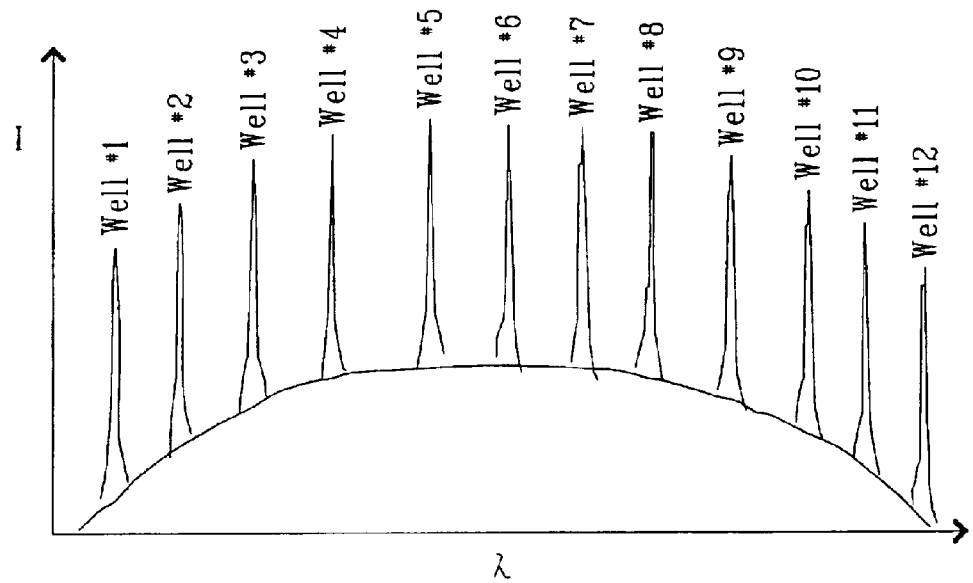
FIG. 10 is a graph illustrating an exemplary optical spectrum from a single spectrometer channel of a multiplexed system shown in FIGS. 9A and 9B.

Referring to FIG. 10, one can see that the present invention makes it possible to adjust the skew angles δs between the RWGs 100 and reading system 120 so as to create a spectrum of resonances $\lambda^-$ and/or $\lambda^+$ that are spaced apart from one another by a distance appropriate for the number of channels required and dynamic range needed for the RWGs 100 and reading system 120. A typical spectral sensitivity of an RWG 100 is 100 nm/RIU (refractive index unit). This means that a RWG 100 which experiences a 0.01 RIU change (considered very large) during the course of the binding of a biological substance 102 produces a 1 nm shift in the location of the spectral resonance $\lambda^-$ and/or $\lambda^+$. In one embodiment, superluminescent diodes 122 (light source 122) can be used to produce intense light beams 126 that have bandwidths of 20–50 nm (3 dB power points). And, a typical spectrometer/CCD system 124 can be used which can support a dynamic range of 50 nm. Thus, even with a reading system 120 that has such a large dynamic range, one could adjust the skew angles δs and pack 20–50 spectral peaks $\lambda^-$ and/or $\lambda^+$ into a single channel without the risk that peaks $\lambda^-$ and/or $\lambda^+$ would interfere with one another during the course of the study. As such referring again to the system shown in FIGS. 9A and 9B, one could use a mere 12 resonance peaks $\lambda^-$ and/or $\lambda^+$ in a spectrum and 8 channels on a spectrometer 124 to interrogate an entire 96 array of RWGs 100 simultaneously without the need for any optical system translation or optical switching. More channels and higher density multiplexing may be used to enable the interrogation of a 384 (16×24) RWG 100 array or larger, or a combination of WDM and TDM techniques may be used to interrogate such an array of RWGs 100.

It should be noted that one can design the reading system 120 to interrogate the double resonances $\lambda^-$ and $\lambda^+$ from each RWG 100 or only a single resonance $\lambda^-$ or $\lambda^+$ from each RWG 100. It follows that if double resonances $\lambda^-$ and $\lambda^+$ from each RWG 100 are used then a larger spectral band would be required to accommodate all of the signals. And, if a single resonance $\lambda^-$ or $\lambda^+$ is used then a smaller spectral band could be used.

It should also be noted that adjustment of the skew angle δ may be used not only for spectral control in order to enable multiplexing, but skew angle δ adjustment may also be used in order to correct manufacturing defects in RWGs 100. For instance, if the grating pitch or waveguide thickness of a particular RWG 100 is out of design specification, than the resonances $\lambda^-$ and $\lambda^+$ will shift from their intended location. Adjustment of the skew angle δ allows one to use the reader system 120 to bring the resonances $\lambda^-$ and $\lambda^+$ back to the desired spectral location. This degree of freedom would be particularly useful if such a design flaw were repeated over many arrays, so that a single adjustment of the reader system 120 corrected the repeated defects in the RWGs 100.

Figure 11:
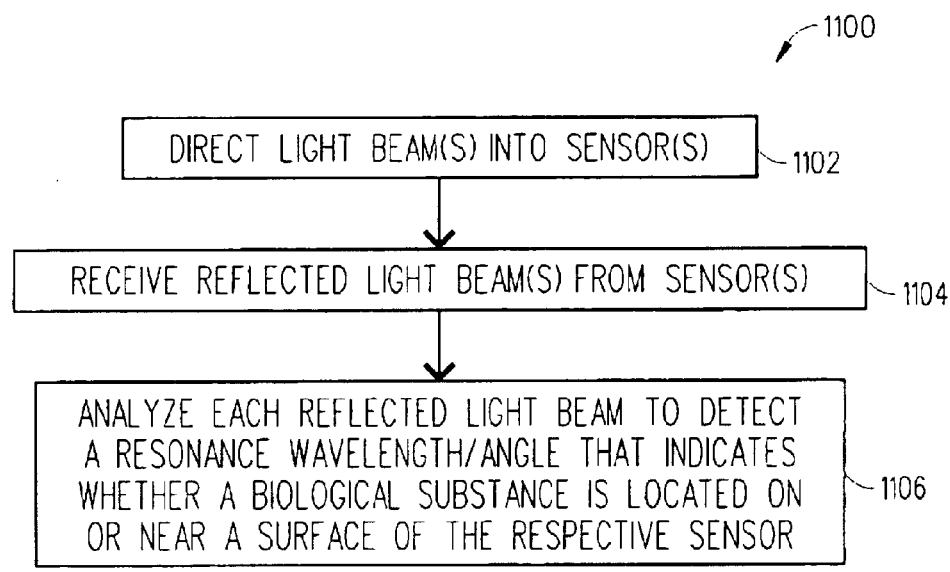
FIG. 11 is a flowchart illustrating the basic steps of a preferred method for using the reading system and RWGs in accordance with the present invention.

Referring to FIG. 11, there is a flowchart illustrating the basic steps of a preferred method 1100 for using the reading system 120 and the RWGs 100 to detect a biological substance 102 in accordance with the present invention. Although the RWGs 100 and reading system 120 are described herein as being used to detect the presence of biological substances 102 like cells, molecules, proteins, drugs, chemical compounds, nucleic acids, peptides or carbohydrates on the surfaces 104 of the RWGs 100, it should be understood that the RWGs 100 and reading system 120 can be used to perform a wide variety of studies. For example, the RWGs 100 and reading system 120 can be used to perform cell migration assays, drug permeability assays, drug solubility studies, virus detection studies and protein secretion studies.

Beginning at step 1102, the light source 124 is used to direct light beam(s) 126 into the RWG(s) 100. At step 1104, the detector 124 receives the reflected light beam(s) 128 from the RWG(s) 100. In one embodiment, the reflected light beams 128 may be multiplexed as described above with respect to FIGS. 9 and 10. Then at step 1106, the detector 124 analyzes each of the received reflected light beams 128 to detect a resonant wavelength or resonant angle which corresponds to a predetermined refractive index that indicates whether the biological substance 102 is located on the surface 104 of the respective RWG 100. Again, each RWG 100 is tuned to have a predetermined spectral resonant condition by adjusting a skew angle δ defined as an angle between a plane of the incident light beam 126 directed into the RWG 100 and a grating vector κ which is perpendicular to lines of the diffraction grating 108 within the RWG 100 (see FIG. 5).

Following are some advantages and uses of the RWGs 100 and reading system 120 of the present invention:

The reader system 120 may be created where one tunes the location of the spectral resonance of a RWG 100 by adjusting the angle of the plane of incidence of the source light 126 makes with the grating vector κ in the RWG 100.

The method may be used to spectrally multiplex multiple signals 128 into a single channel to be read by a spectrometer or other spectral resolving instrument 124.

The multiplexed system of an array of RWGs 100 and the reading system 120 reduces or eliminates the need to time division multiplex the sensor signals 128 which reduces the cost and complexity of the system.

The adjustment of the skew angle δ may also be used to correct for defects in the design of RWGs 100 which place the spectral resonances $\lambda^-$ and/or $\lambda^+$ in non-optimal locations.

From the foregoing, it can be readily appreciated by those skilled in the art that the present invention may be used to spectrally multiplex optical signals received from resonant grating waveguide sensors. The ability to multiplex optical signals is important because it enables a practical high throughput system to be fabricated using an array of sensors. It should also be appreciated that described herein are techniques that can be used to spectrally control and multiplex signals by adjusting only the optical illumination system, thus obviating any requirements for precise individual fabrication of the sensors. And, the use of WDM technology enables many sensors signals to be interrogated simultaneously, taking better advantage of system optical power, reducing overall array read time, and reducing the mechanical complexity of the overall reader system.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A reading system comprising:
    a light source for directing a light beam into a grating-based waveguide sensor; and
    a detector for receiving a reflected light beam from the grating-based waveguide sensor that was tuned to have a resonance at a predetermined spectral location by adjusting a skew angle defined as an angle between a plane of incidence of the light beam directed into the grating-based waveguide sensor and a grating vector which is perpendicular to lines of a diffraction grating within the grating-based waveguide sensor, wherein said detector is used to analyze the reflected light beam so as to detect a resonant condition which corresponds to a predetermined refractive index that indicates whether a biological substance is located on a surface of the grating-based waveguide sensor.

2. The reading system of claim 1, wherein said biological substance is a cell, molecule, protein, drug, chemical compound, nucleic acid, peptide or carbohydrate.

3. The reading system of claim 1, wherein said detector utilizes an angular interrogation approach to analyze the reflected light beam and enable the detection of an resonant angle which indicates whether the biological substance is located on the surface of the grating-based waveguide sensor.

4. The reading system of claim 1, wherein said detector utilizes a spectral interrogation approach to analyze the reflected light beam and enable the detection of a resonant wavelength which indicates whether the biological substance is located on the surface of the grating-based waveguide sensor.

5. The reading system of claim 1, further comprises a plurality of grating-based waveguide sensors wherein each of the grating-based waveguide sensors is tuned to have a resonance at a predetermined spectral location by adjusting the respective skew angle which enables spectral multiplexing of a plurality of the reflected light beams.

6. The reading system of claim 1, wherein said skew angle is adjusted by rotating the grating-based waveguide sensor while maintaining the angle of the plane of incidence of the light beam emitted from said light source.

7. The reading system of claim 1, wherein said skew angle is adjusted by moving the angle of the plane of incidence of the light beam emitted from said light source while maintaining the position of the grating-based waveguide sensor.

8. The reading system of claim 1, wherein said skew angle is adjusted to correct a manufacturing defect in the grating-based waveguide sensor.

9. A reading system capable of performing a multiplexed interrogation of an array of grating-based waveguide sensors, said reading system comprising:
a light source;
at least one collimator lens, each collimator lens capable of directing a light beam emitted from said light source into one of the grating-based waveguide sensors and further capable of receiving a reflected light beam from the one grating-based waveguide sensor, wherein each of the grating-based waveguide sensors was tuned to have a resonance at a desired spectral location by adjusting a skew angle ($\delta$) defined by the equation:

$$\sin\theta\cos\delta = n_{\mathit{eff}} - \frac{\lambda}{\Lambda}$$

where $\theta$ is an angle of incidence of the respective light beam, $n_{\mathit{eff}}$ is the index of refraction of the grating-based waveguide sensors, $\lambda$ is the wavelength of the respective light beam, $\Lambda$ is the grating period;
a dispersive device capable of receiving a plurality of the reflected light beams from said collimating lenses and further capable of detecting a resonant wavelength/angle in the respective reflected light beams which corresponds to a predetermined refractive index that indicates whether a biological substance is located on a surface of the respective grating-based waveguide sensor.

10. The reading system of claim 9, wherein said biological substance is a cell, molecule, protein, drug, chemical compound, nucleic acid, peptide or carbohydrate.

11. The reading system of claim 9, wherein said dispersive device is a spectrometer.

12. The reading system of claim 9, wherein each skew angle is adjusted by rotating an angle of the plane of incidence of the light beam emitted from said respective collimating lens while maintaining the position of the respective grating-based waveguide sensor.

13. The reading system of claim 9, wherein said grating-based waveguide sensors are tuned to have spectral locations that are separated from one another a predetermined distance to enable said dispersive device to detect the presence of the biological substance located on the surface of any one of the set of grating-based waveguide sensors.

14. A method for interrogating one or more grating-based waveguide sensors, said method comprising the steps of:
directing a light beam into each grating-based waveguide sensor;
receiving a reflected light beam from each grating-based waveguide sensor; and
analyzing each received reflected light beam to detect a resonant condition which corresponds to a predetermined refractive index that indicates whether a biological substance is located on a surface of the respective grating-based waveguide sensor, wherein each grating-based waveguide sensor was tuned to have a resonance at a predetermined spectral position by adjusting a skew angle defined as an angle between a plane of incidence of the light beam directed into that grating-based waveguide sensor and a grating vector which is perpendicular to lines of a diffraction grating within that grating-based waveguide sensor.

15. The method of claim 14, wherein said biological substance is a cell, molecule, protein, drug, chemical compound, nucleic acid, peptide or carbohydrate.

16. The method of claim 14, wherein said analyzing step utilizes an angular interrogation approach to analyze each reflected light beam and enable the detection of an resonant angle which indicates the presence of the biological substance on the surface of each grating-based waveguide sensor.

17. The method of claim 14, wherein said analyzing step utilizes a spectral interrogation approach to analyze each reflected light beam and enable the detection of a resonant wavelength which indicates the presence of the biological substance on the surface of the each grating-based waveguide sensor.

18. The method of claim 14, wherein each skew angle was adjusted by moving the angle of the plane of incidence of the light beam while maintaining the position of the respective grating-based waveguide sensor.

19. The method of claim 14, wherein each skew angle was adjusted by rotating the respective grating-based waveguide sensor while maintaining the angle of the plane of incidence of the light beam.

20. The method of claim 14, wherein said grating-based waveguide sensors are interrogated by multiplexing a predetermined number of reflected light beams.

21. The method of claim 14, wherein said grating-based waveguide sensors are located in wells formed within a microplate.

22. A microplate comprising:
a frame including a plurality of wells formed therein, each well incorporating a grating-based waveguide sensor that was tuned to have a resonance at a desired spectral location by adjusting a skew angle ($\delta$) defined by the equation:

$$\sin\theta\cos\delta = n_{eff} - \frac{\lambda}{\Lambda}$$

where θ is an angle of incidence of a light beam directed into the grating-based waveguide sensor, $n_{eff}$ is the index of refraction of the grating-based waveguide sensor, λ is the wavelength of the light beam, Λ is the grating period.

23. The microplate of claim 22, wherein a reading system is used to interrogate each of the grating-based waveguide sensors by:

directing a light beam into each grating-based waveguide sensor, receiving a reflected light beam from each grating-based waveguide sensor; and analyzing each received reflected light beam to detect a resonant condition which corresponds to a predetermined refractive index that indicates whether the presence of the biological substance is on a surface of the respective grating-based waveguide sensor.

24. The microplate of claim 23, wherein said biological substance is a cell, molecule, protein, drug, chemical compound, nucleic acid, peptide or carbohydrate.

* * * * *